United States Patent [19]

VandenBerg

[11] Patent Number: Plant 7,019

[45] Date of Patent: Sep. 5, 1989

[54] CHRYSANTHEMUM PLANT NAMED NEVADO

[75] Inventor: Cornelis P. VandenBerg, Salinas, Calif.

[73] Assignee: Yoder Brothers, Inc., Barberton, Ohio

[21] Appl. No.: 210,004

[22] Filed: Jun. 22, 1988

[51] Int. Cl.[4] ..... A01H 5/00

[52] U.S. Cl. ..... Plt./74

[58] Field of Search ..... Plt./74

*Primary Examiner*—James R. Feyrer

[57] ABSTRACT

A chrysanthemum plant named Nevado particularly characterized by its flat capitulum form; daisy capitulum type; white ray floret color; diameter across face of capitulum of up to 7 cm at maturity; uniform nine week photoperiodic flowering response to short days; medium plant height when grown single stem; 12 to 20 cm peduncles on open, terminal sprays; and excellent tolerance to low temperatures for bud initiation and flower development.

3 Drawing Sheets

The present invention comprises a new and distinct cultivar of chrysanthemum, botanically known as *Dendranthema grandiflora,* and referred to by the cultivar name Nevado.

Nevado, identified as 83-716009, was originated from a cross made in a controlled breeding program in Salinas, Calif. in 1983.

The female parent and the male parent of Nevado were both unnamed seedlings, identified respectively as 78-592007 and 79-L62003.

Nevado was discovered and selected as one flowering plant within the progeny of the stated cross by Cornelis P. VandenBerg in December 1983 in a controlled environment in Bogota, Colombia.

The first act of asexual reproduction of Nevado was accomplished when vegetative cuttings were taken from the initial selection in March 1984 in a controlled environment in Bogota, Colombia by technicians working under formulations established by Cornelis P. VandenBerg.

Horticultural examination of controlled flowerings of successive plantings has shown that the unique combination of characteristics as herein disclosed for Nevado are firmly fixed and are retained through successive generations of asexual reproduction.

Nevado has not been observed under all possible environmental conditions. The phenotype may vary significantly with variations in environment such as temperature, light intensity, and daylength.

The following observations, measurements and comparisons describe plants grown in Salinas, Calif. under greenhouse conditions which approximate those generally used in commercial greenhouse practice. The low temperature tolerance was determined by repeating flowerings in Bogota, Colombia.

The following traits have been repeatedly observed and are determined to be basic characteristics of Nevado, which, in combination, distinguish this chrysanthemum as a new and distinct cultivar:

1. Flat capitulum form.
2. Daisy capitulum type.
3. White ray floret color.
4. Diameter across face of capitulum up to 7 cm at maturity.

5. Uniform nine week photoperiodic flowering response to short days.
6. Peduncle length ranging from 12 to 20 cm on open terminal sprays.
7. Medium plant height, requiring two long day weeks prior to short days to attain a flowered plant height of 100 to 110 cm for year-round flowerings.
8. Excellent tolerance to low temperatures for bud initiation and flower development.

The accompanying photographic drawings show typical inflorescence and leaf characteristics of Nevado, with the colors being as nearly true as possible with illustrations of this type. Sheet 1 is a color photograph of Nevado grown as a single stem cut spray mum. Sheet 2 is a black and white photograph of three views of the inflorescence of Nevado. Sheet 3 is a black and white photograph showing the upper and under sides of the leaves of Nevado at three stages of development (mature, intermediate and immature).

Of the commercial cultivars known to the inventor, the most similar in comparison to Nevado is White Marble. Reference is made to attached Chart A, which compares certain characteristics of Nevado to the same characteristics of White Marble.

Similar traits are ray floret color, capitulum form and type, plant height and flowering response period. The peduncle length of Nevado is shorter than that of White Marble. Nevado has a smaller diameter of capitulum than White Marble. Under adverse conditions White Marble exhibits compounding of the spray formation and develops bract tissue in the disc. The spray formation of Nevado is always terminal, with no development of bracts.

In the following description, color references are made to The Royal Horticultural Society Colour Chart. The pure white ray floret color of Nevado is not represented in The Royal Horticultural Society Colour Chart. The color values were determined on plant material grown in Salinas, Calif. on Apr. 22, 1988.

Classification:

*Botanical.*—*Dendranthema grandiflora,* cv Nevado.

*Commercial.*—Daisy cut spray mum.

INFLORESCENCE

A. Capitulum:
*Form.*—Flat.
*Type.*—Daisy.
*Diameter across face.*—Up to 7 cm at maturity.

B. Corolla of ray florets:
*Color (general tonality from a distance of three meters).*—White.
*Color (upper surface).*—White.
*Color (under surface).*—White.
*Shape.*—Straight, slightly ribbed. Crossection slightly concave.

C. Corolla of disc florets:
*Color (mature).*—Closest to 7A.
*Color (immature).*—144C.

D. Reproductive organs:
*Androecium.*—Present on disc florets only; no pollen.
*Gynoecium.*—Present on both ray and disc florets.

PLANT

A. General appearance:
*Height.*—Medium; 100 to 110 cm as a single stem cut mum with 14 long days prior to short days.

B. Foliage:

*Color (upper surface).*—147A.
*Color (under surface).*—147B.
*Shape.*—Deeply lobed and slightly serrated.

CHART A

COMPARISON OF NEVADO AND WHITE MARBLE

| | Nevado | White Marble |
|---|---|---|
| Ray floret color | White | White |
| Capitulum form and type | Flat Daisy | Flat Daisy |
| Spray formation | Terminal 12 to 20 cm peduncles | Terminal to compound 20 to 25 cm peduncles |
| Diameter across face of capitulum | Up to 7 cm | Up to 9 cm |
| Plant height | Medium | Medium |
| Flowering response period | 9 weeks | 9 weeks |
| Low temperature tolerance | Excellent | Good |

COMPARISONS MADE OF PLANTS GROWN AS SINGLE STEM SPRAY CUT MUMS IN SALINAS, CALIFORNIA

I claim:

1. A new and distinct chrysanthemum plant named Nevado, as described and illustrated.

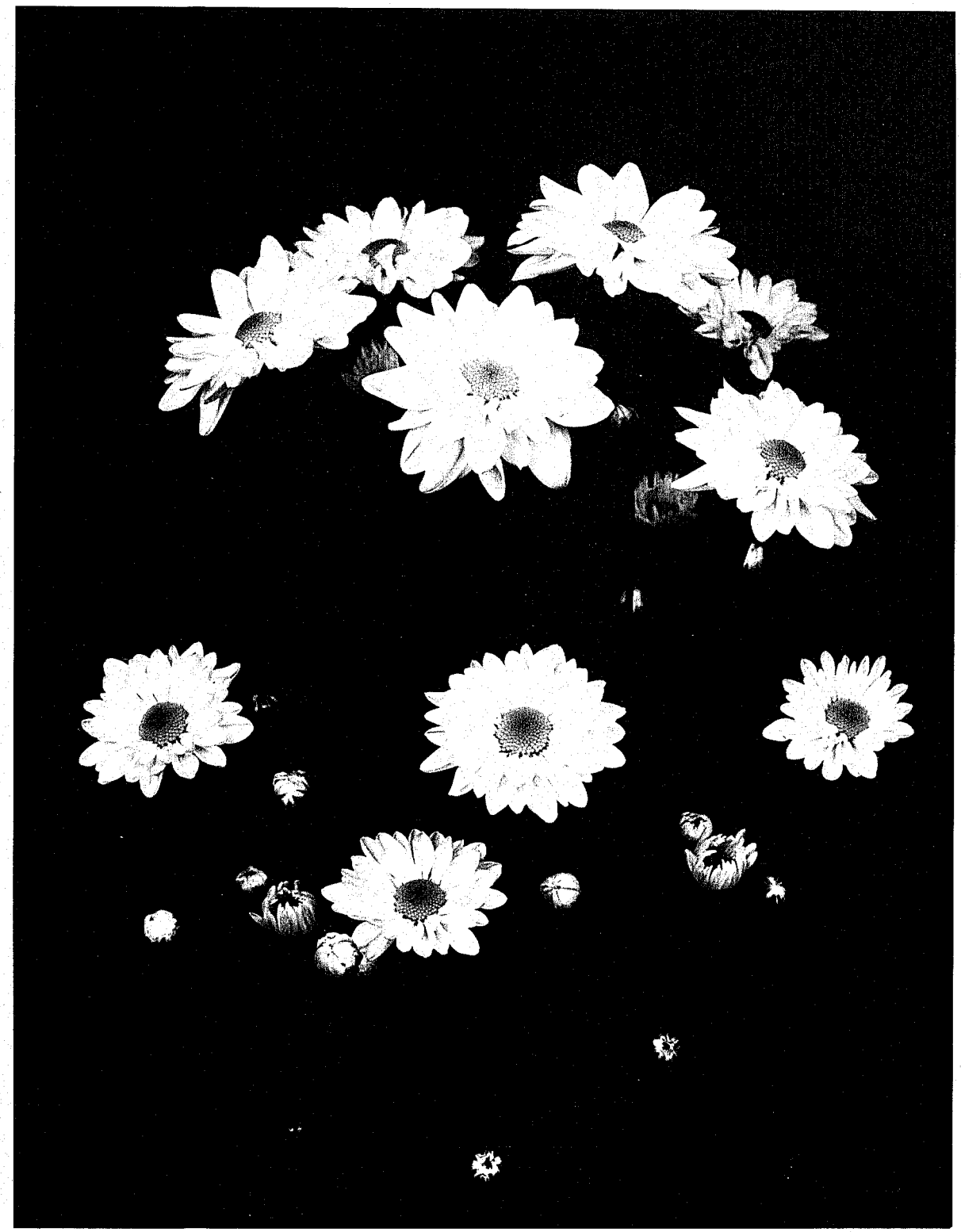

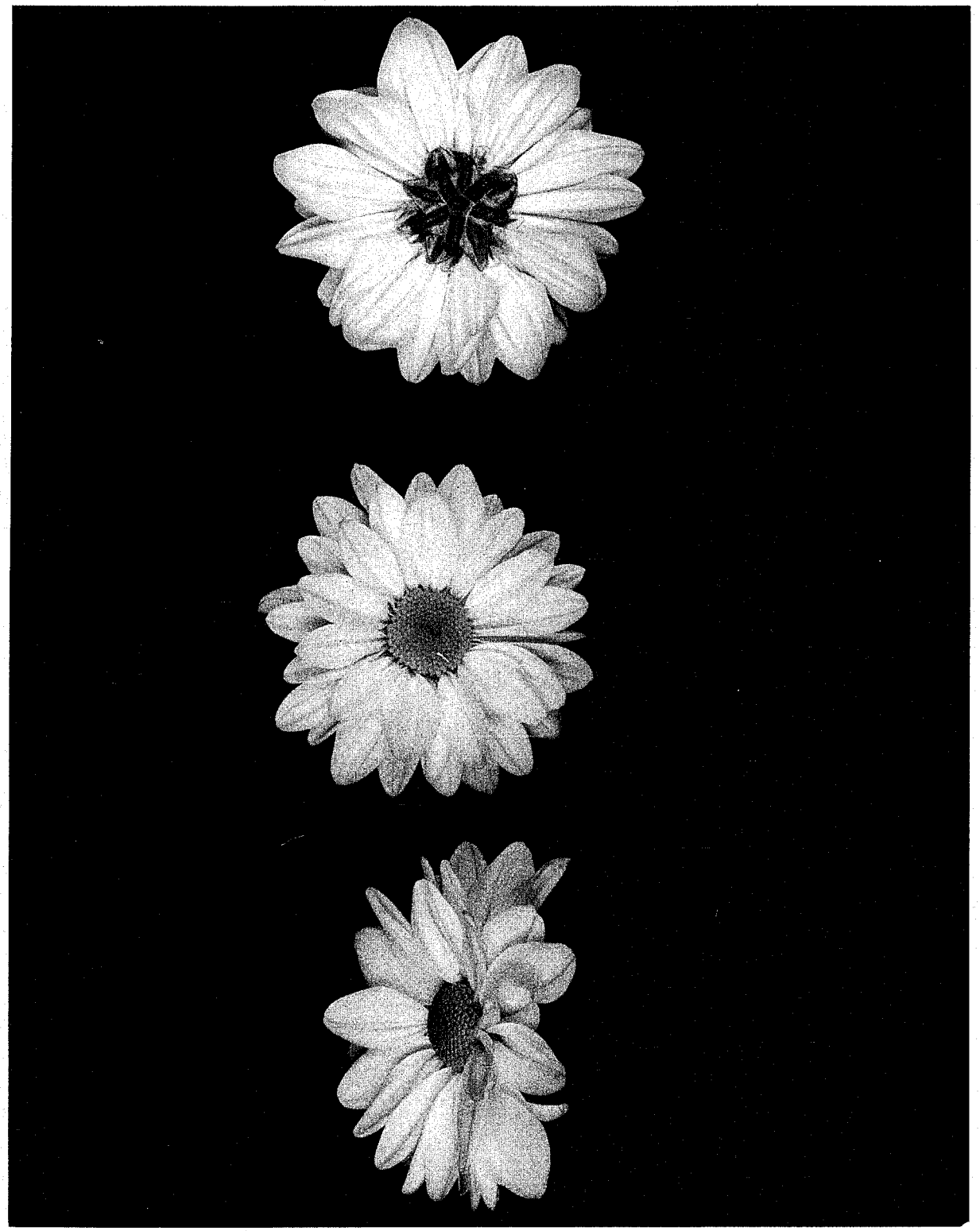

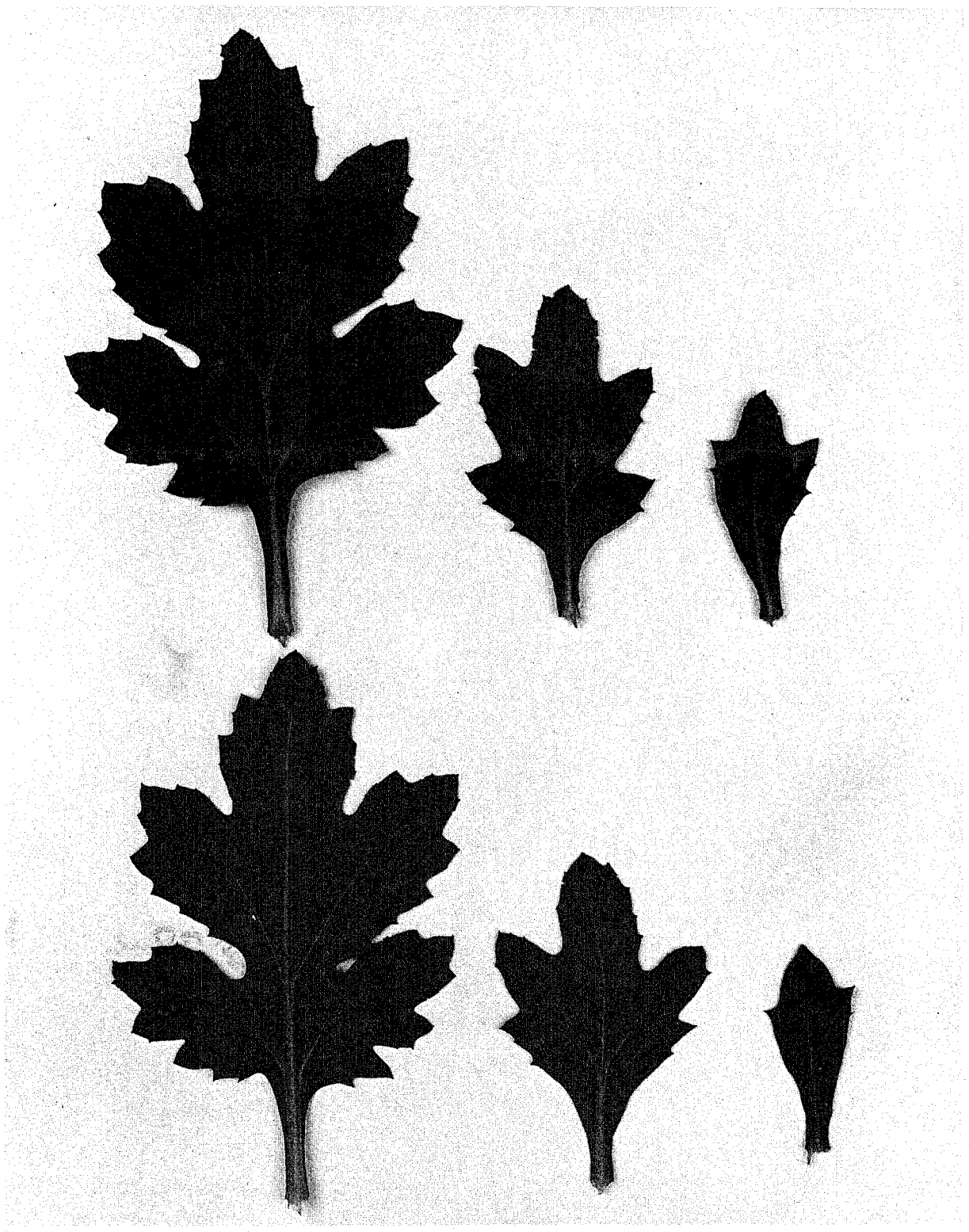

* * * * *